(12) United States Patent
Bjellqvist et al.

(10) Patent No.: US 7,964,075 B2
(45) Date of Patent: Jun. 21, 2011

(54) ELECTRODIC BRIDGE

(75) Inventors: Bengt Bjellqvist, Uppsala (SE); Kristina Uhlen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 264 days.

(21) Appl. No.: 12/296,963

(22) PCT Filed: Apr. 20, 2007

(86) PCT No.: PCT/SE2007/000378
§ 371 (c)(1),
(2), (4) Date: Oct. 13, 2008

(87) PCT Pub. No.: WO2007/126354
PCT Pub. Date: Nov. 8, 2007

(65) Prior Publication Data
US 2010/0163416 A1  Jul. 1, 2010

(30) Foreign Application Priority Data
Apr. 27, 2006  (SE) ...................... 0600970

(51) Int. Cl.
*G01N 27/453*  (2006.01)
(52) U.S. Cl. ........................... 204/548; 204/459
(58) Field of Classification Search ................ 204/459, 204/438, 610, 644, 548
See application file for complete search history.

(56) References Cited

U.S. PATENT DOCUMENTS

| | | | |
|---|---|---|---|
| 4,130,470 A | 12/1978 | Rosengren et al. | |
| 5,082,548 A * | 1/1992 | Faupel et al. | 204/644 |
| 7,601,251 B2 * | 10/2009 | Rooney et al. | 204/548 |
| 2004/0079638 A1 | 4/2004 | Rooney et al. | |
| 2004/0222096 A1 | 11/2004 | Herbert | |
| 2005/0006239 A1 | 1/2005 | Amshey et al. | |

FOREIGN PATENT DOCUMENTS

| | | |
|---|---|---|
| EP | 0 287 513 | 10/1988 |
| EP | 1564550 | 8/2005 |
| WO | WO01/20315 | 3/2001 |
| WO | WO01/86279 | 11/2001 |
| WO | WO02/26773 | 4/2002 |
| WO | WO03/029523 | 4/2003 |
| WO | WO03/101592 | 12/2003 |
| WO | WO 2005/021841 | 3/2005 |
| WO | WO2005/062032 | 7/2005 |
| WO | WO2006/036119 | 4/2006 |

(Continued)

OTHER PUBLICATIONS

Hackler et al. "Flattening and/or expanding of pH gradients in isoelectric focusing glens exemplified with PhastSystem," Electrophoresis 1988, 9, 262-267.*

(Continued)

*Primary Examiner* — Alex Noguerola
(74) *Attorney, Agent, or Firm* — Yonggang Ji

(57) ABSTRACT

The present invention relates to an electrode bridge or sample application bridge for use in electrophoresis, preferably isoelectric focusing, IEF. More closely, the invention relates to an electrodic bridge or sample loading bridge for preventing denaturant depletion from the IPG (immobilized pH gradient) gel and, optionally, for loading samples onto the IPG gel. The pH of the bridge is adjustable for adoption to positioning at the acid as well as basic end of the IPG strips.

11 Claims, 1 Drawing Sheet

FOREIGN PATENT DOCUMENTS

WO    WO 2007/073293    6/2007

OTHER PUBLICATIONS

Colin Simpson, Chapter 12—Analytical Electrophoresis, from Characterization of Proteins, Biological Methods, published by Human Press, 1988, 339-363.*

Bjellqvist, B., et al., Journal of Biochemical and Biophysical Methods, 6 (1982) 317-339.
Kohlheyer, D., et al., Lab Chip, 6(3) (2006) 374-380.
Sabounchi-Schutt, F., et al., Electrophoresis 2000, 21(17) (2000) 3649-3656.

* cited by examiner

ELECTRODIC BRIDGE

CROSS-REFERENCE TO RELATED APPLICATIONS

This application is a filing under 35 U.S.C. §371 and claims priority to international patent application number PCT/SE2007/000378 filed Apr. 20, 2007, published on Nov. 8, 2007, as WO 2007/126354, which claims priority to patent application number 0600970-8 filed in Sweden on Apr. 27, 2006.

FIELD OF THE INVENTION

The present invention relates to an electrode bridge or sample application bridge for use in electrophoresis, more precisely isoelectric focusing, IEF. The invention relates to an electrodic bridge for preventing denaturant depletion from the IPG (immobilised pH gradient) gel and, optionally, for loading samples onto the IPG gel. The pH of the bridge is adjustable for adoption to the pH of the acidic or basic end of the IPG gel.

BACKGROUND OF THE INVENTION

One type of widely used electrophoresis is isoelectric focussing, wherein substances, such as proteins, are separated according to their pI-value. For isoelectric focussing, sample loading has traditionally been performed by cup loading by placing a cup on the gel and letting a sample pass through the cup into the gel. The cup is positioned on the gel for the whole electrophoresis run.

Alternatively for dried gels, the sample may be mixed with electrophoresis buffer and used as a rehydration solution to rehydrate the dried gel, such as Immobiline DRYSTRIP™ gels.

More recently, sample application paper in the form of conventional filter paper, has been placed between the electrode and the electrophoresis gel to load a sample into an electrophoretic gel. This functions satisfactorily for sample application from the anode side of the gel. However, this approach does not work when using acidic pH intervals extending to pH-values bellow pH 4, for example a pH 3-11 strip, a pH 3-7 or a pH 3-5 strip. When samples are paper loaded from the anodic (acidic) side of the IPG strip, the proteins and peptides will be retained in the paper As an alternative, rehydration loading can be used in these pH intervals. However, rehydration loading is not possible with swollen gels, such as pre-swollen RTG (ready-to-go) strips. Thus, these kind of gels need an alternative loading, especially for application of large samples which is very difficult today.

The co-pending application WO 05/062032 provides an alternative way to load samples onto electrophoretic IPG gels which avoids the problem with protein precipitation.

This invention enables sample loading from the cathode side of the IPG gel or strip. According to this invention, the sample is applied to an acidic interval IPG gel or strip, such as a RTG (ready-to-go) strip. This novel application enables sample loading in preparative amounts of protein. This is achieved by providing use of a positively charged support for sample application from the cathode side of the gel.

In spite of this improvement over prior art, there is still a need of alternative ways of sample loading onto electrophoretic gels.

SUMMARY OF THE INVENTION

The present inventors have found that, during isoelectric focusing, urea (or other denaturant) in the gel will disappear from the IPG (Immobilised pH gradient) gel due to osmotic pumping. The loss of urea from the IPG gel affects the isoelectric focusing as urea influences the pH of the acidic part of the strip in a negative way and this leads to blurred pI-spots in the gel and an uncontrolled, non-reproducible pH-gradient along the gel after finished focusing.

The present invention provides a novel type of electrode bridge comprising high concentrations of denaturant and buffering capacity. Besides preventing denaturant depletion from the IPG-gel, the electrode bridge of the invention may also be used for sample loading.

Thus, in a first aspect, the invention relates to an electrode bridge for connection between an anodic or cathodic electrode and one end of an IPG gel, wherein the electrode bridge is provided with denaturant and pH-adjusting groups. The pH-adjusting groups are, just as IPG s, bound to the backbone or matrix forming the electrode bridge. In a case of a gel-bridge composed of a polyacrylamide gel the pH-adjusting groups are bound to the polyacrylamide network and in a gelbridge composed of paper the groups are bound to the cellulose fibers. The pH resulting in an anodic electrode bridge, when low molecular weight salt and buffer ions not bound to the matrix have been transported away by the electric field, should become equally acidic or more acidic than the most acidic part of the IPG gel. On the other hand the pH resulting in a basic bridge, becomes after finished focusing equally basic or more basic than the most basic part of the IPG gel.

Thus, the pH in the bridge after focusing depends on the pH interval of the applied IPG gel.

An anodic bridge is an electrode bridge positioned between the anode and the anode end of an electrophoresis gel and a cathodic electrode bridge is a bridge positioned between the cathode and the cathode end of the electrophoresis gel.

The pH-adjusting groups enable either acidification of the gel bridge, in which case the gel bridge is used from the anodic side or basification of the gel bridge, in which case the gel bridge is used from the cathode side. This pH-adjustment prevents loss of proteins/peptides when the electrode bridge is also used for sample application to IPG gels.

According to the invention the electrode bridge is preferably provided with acidic groups and is located between the anode and the anode side of the electrophoretic gel.

The acidic groups are selected from strong acids, such as sulphonic acid, sulphonic acid esters, phosphonic acid and carboxylic acids with pK-values lower than 5. Examples of compounds suitable to use for incorporation of carboxylic acid groups in polyacrylamide gels are acrylic acid, 2-acrylamido glycolic acid, N-acryloyl glycine and 3-acrylamido propanoic acid. On important feature of the electrode bridge according to the invention, is that it should have a buffering capacity which requires that the acidic groups should comprise one group with a pK-value, which is less than one pH-unit away from the pH resulting in the gel bridge and more preferably the pK-value should be less than 0.6 pH units away from the resulting pH-value. An electrode bridge could contain solely one buffering acidic group in an amount which preferably is high enough to adjust the resulting pH-value in the bridge to a value equal or lower than the pH-value of the acidic end of the IPG-strip.

Preferably, the IPG gel is an acidic interval IPG gel and the pH of the bridge is equal or lower than the most acidic pH of the gel. Preferably the pH is approximately equal in the bridge and IPG-gel.

Alternatively, the electrode bridge is provided with basic groups and located between the cathode and the cathode side of the electrophoretic gel.

The electrode bridge is preferably made of a hydrogel such as polyacrylamide or derivatised polyacrylamide, polyvinyl alcohol or agarose, but may also be made of a cellulose based material, such as paper or Wettex, or a monolith.

In a preferred embodiment, the IPG gel comprises an acidic interval (below pH 4) IPG gel or strip.

The electrodic bridge may be an anodic bridge made of cellulose-based material provided with sulphonic acid groups. Preferably, the electrodic bridge is an anodic bridge made of polyacrylamide provided with acid acrylamido derivatives.

When the gel bridge is used as sample applicator, it may be used in analytical as well as preparative amounts.

The electrode bridge may be used for application of samples to IPG gels per se or used for 2D gels, wherein the first dimension is isoelectric focussing and the second dimension is according to molecular weight. A preferred use is for isoelectric focussing of peptides as a pre-step for later identification thereof, by for example mass spectrometry.

In a second aspect the invention relates to use of an electrode bridge as described above for isoelectric focusing of protein and/or peptides.

In a third aspect, the invention relates to a kit comprising one or more electrode bridge(s) as described above one or more IPG gel(s). The IPG gel is preferably an IPG gel comprising an acidic interval (pH below 4), such as pH 3.5-5, pH 3.5-4.5, pH 4-5 or pH 3-10.

In a preferred embodiment, the kit comprises an anodic bridge comprising polyacrylamide provided with acid acrylamido derivatives.

The electrode bridge is provided between one end of the gel, i.e. the anodic end or the cathodic end, and one of the electrodes, i.e. anode or cathode, and prevents denaturant depletion from the IPG gel. The type of denaturant is dependent on the type of denaturant used in the gel. The sample bridge is preferably saturated a high denaturant concentration, such as with 8M urea. If the electrode bridge is provided on the anodic side of the IPG gel, then an anodic electrode bridge is used. If the electrode bridge is provided on the cathodic side of the IEF gel, then a basic electrode bridge is used.

DETAILED DESCRIPTION OF THE INVENTION

Figure 1:
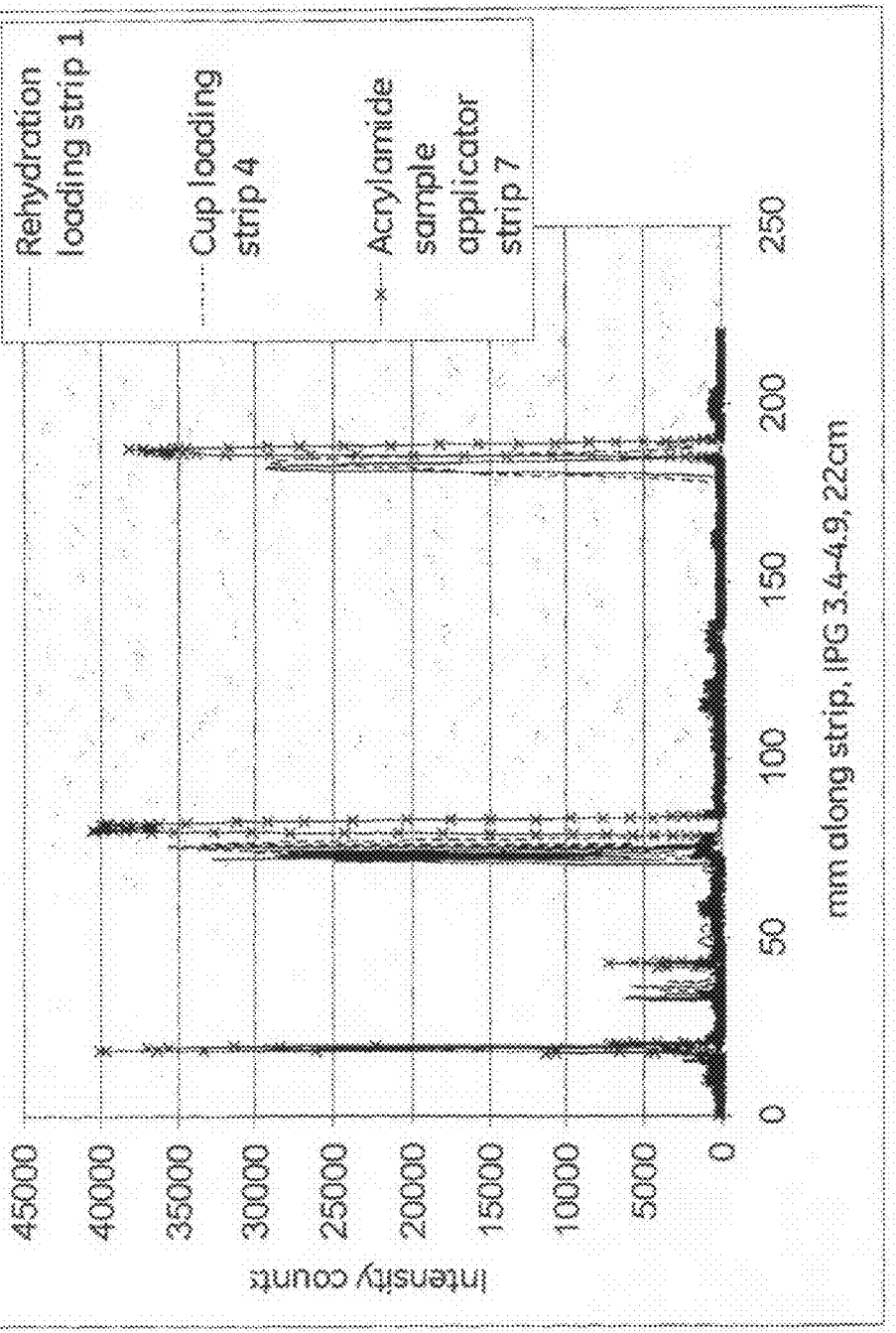
FIG. 1 shows a comparison of detected amount pI-markers when using different sample application methods, wherein the solid line represents rehydration loading, the dotted line represents cup loading and the x-x-x line represents sample loading with a gel bridge according to the present invention.

The present invention provides novel type of electrode bridge. According to the invention the electrode bridge has high water absorbing capacity. Preferably electrode bridge should, depending on the application be able to hold sample volumes, varying from 50 μl to 10000 μl. When used for sample application, protein and/or peptide concentrations used can fall in the region 0.1 mg/ml to 100 mg/ml, but most commonly the concentrations will fall in the region 0.5-5 mg/ml. The electrode bridge must be substantially inert to the substances, such as proteins, present in the sample.

The thickness of the support depends on the bridge material. The dimensions of the support are determined by the size of the gel and the sample amount.

The electrophoretic bridge according to the invention may be used in association with any swollen electrophoretic gel, preferably an IPG gel.

When the bridge is used as a sample applicator, the sample is added to the bridge and thereafter it is placed between the anode or cathode and the electrophoresis gel. At one end the bridge is in contact with the electrode and at the other end in contact with the gel. The running conditions are the same as for any IPG run or 2D electrophoresis run.

When using conventional cup loading, there are often disturbances in the first 15% of the gradient due to the presence of the cup. For short IPG strips this may be a very significant portion of the gel. With the present invention this problem is avoided.

The sample may be loaded in analytical or preparative amounts. The sample may be a biological sample or any other sample. The present invention is especially suited for peptide focusing with later identification by for example mass spectrometry.

Experiment 1: Production of Electrode Bridge
a) Cellulose Based Bridge

Below the procedure to introduce sulphonic acid groups on the surface of paper or a Wettex cloth is described:

1.1 g NaOH is dissolved in 62.5 ml MQ-water in a 200 ml broad necked E-flask. Thereafter, 37.5 ml VSA (vinyl sulphonate sodium) is added. Pieces of paper or Wettex cloth were put into the flask and the flask was covered with parafilm and immersed into a water bath of 50° C. The reaction was allowed to proceed over night. The reaction solution was poured off and the paper or Wettex cloth was rinsed with MQ-vatten 4 times and then allowed to stand in water for 48 hours. The rinsing water then had a pH of about 5.

b) Gel Based Bridge

An immobilized pH-plateau gel is cast by mixing a solution of acrylamide monomers with a cross-linking reagent and a mixture of immobilines, and let them co-polymerize, usually with the help of chemical inducement/catalysis.

The electrode gel bridge used in the described Experiment 2 below, was cast from a immobiline mixture of pH 3.3 with the following protocol and composition:

| Vol % | pH | Glycerol % |
|-------|------|------------|
| 0.00  | 3.30 | 20         |
| 100   | 3.30 | 20         |

Recipe Immobiline Solution pH 3.3:

| Raw material: | DEST | pK 3.6 | pK 4.6 | pK 6.2 | pK 9.3 | Tris | Dest. |
|---|---|---|---|---|---|---|---|
| Batch: |  | 307878 | 303759 | 309884 | 310118 |  |  |
| Conc (M): |  | 0.200 | 0.201 | 0.200 | 0.198 | 1.00 |  | to

-continued

| Raw material: | DEST | pK 3.6 | pK 4.6 | pK 6.2 | pK 9.3 | Tris | Dest. |
|---|---|---|---|---|---|---|---|
| Calculated amount: | 167 | 69.81 | 34.25 | 60.38 | 23.22 | 12.07 | 500 |
| Unit: | | gram | Gram | gram | gram | ml | ml |

Crosslinker: methylenebisacrylamide
Catalysts: TEMED and PERS

Experiment 2: Comparison of Different Sample Application Procedures for Isoelectric Focusing A comparison of different sample application procedures was performed. The methods compared were rehydration loading, cup loading and sample application by the electrode bridge according to the present invention in the form of a polyacrylamide gel sample applicator with pH 3.5. The detectable amounts of the different fluorescent pI-markers were compared after focusing.

5 μg of a tryptic digest sample from *Saccharomyces cerevisiae*, Type II, was mixed with ~0.5 μg of each of the pI-markers '3.86', '4.25' and '4.54', below called the sample solution. A 'pI-marker' is a fluorescently labelled peptide with known isoelectric point that can be detected by fluorescence scanning. The fluorescent label used was CY5™ (available from Amersham Biosciences AB; Sweden) which emission spectrum is taken at ~660 nm (ETTAN™ DIGE System—User Manual, Amersham Biosciences AB, Sweden).

A 22 cm IPG peptide strip (pH 3.4-4.9) was rehydrated overnight (~15 hours, room temperature) in 250 μl of 8M urea and 1% IPG buffer 2.5-5. For the rehydration loading experiment, the sample solution was also included in the solution for strip rehydration.

The sample application gel bridge (cut from a larger gel to size 40×8×1 mm) was rehydrated overnight (~15 hours, room temperature) in 330 μl of 8M urea and sample solution. The rehydrated strip was transferred to an ETTAN™ IPG-PHOR™ manifold.

For the cup loading experiment, the sample solution was added to a cup on the basic end of the strip.

Paper bridges with 300 μl of 8M urea were used on the acidic end of the strips, in the cases where sample was applied with rehydration loading or cup loading, to prevent the urea concentration in the strip to decrease during focusing.

Isoelectric focusing was run using the following program: Gradient 500 V 1 minute, Gradient 4000 V 3 hours, Gradient 6000 V 3 hours, Gradient 10000 V 3 hours, Step 10000 V 12 hours (total ~100 kVhrs). ETTAN™ IPGPHOR™ II was used as the focusing unit and the focusing was performed at 20° C.

After focusing, the IPG strip was scanned in a fluorescence scanner (TYPHOON™ 9400 scanner, Amersham Biosciences, Sweden) at 660 nm, to determine the exact position and intensity of the fluorescent pI-markers. The same intensity of the laser was used for all scans, 330PMT. The TYPHOON™ pictures were evaluated in IMAGEQUANT™ and fluorescence intensity graphs established.

Results

FIG. 1 shows a comparison between the fluorescence intensity graphs of the different sample application methods.

From the results, it appears that the acidic pI-marker only is present in very limited amounts when sample is applied by rehydration loading or cup loading. When sample is applied by the acidic acrylamide gel sample applicator bridge with pH~3.5 the pI-marker is present in equal amounts as the other pI-markers.

It also appears from the results that an over all higher amount of pI-markers is detected in the strips where the sample is applied by the acidic acrylamide gel sample applicator bridge having pH~3.5.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An electrode bridge for positioning between an anodic or cathodic electrode and one end of an IPG (Immoblised pH gradient) gel for isoelectric focusing, wherein the electrode bridge is provided with denaturant and pH-adjusting groups, and wherein, for an anodic bridge, the pH after finished focusing is equal or more acidic than the lowest pH of the IPG-gel, and wherein, for a cathodic bridge, the pH after finished focusing is equal or more basic than the highest pH of the IPG-gel.

2. The electrode bridge of claim 1, wherein the bridge is provided with acidic groups and is positioned between the anode and the anode side of the IPG gel.

3. The electrode bridge of claim 2, wherein the acidic groups are selected from sulphonic acid, sulphonic acid derivatives, phosphonic acid, and carboxylic acids or a combination thereof.

4. The electrode bridge of claim 1, wherein the pH of the bridge is approximately equal as the lowest or highest pH of the IPG gel.

5. The electrode bridge of claim 1, wherein the bridge is provided with basic groups and is positioned between the cathode and the cathode side of the IPG gel.

6. The electrode bridge of claim 1, wherein the electrode bridge is made of hydrogel, a cellulose based material, or a monolith.

7. The electrode bridge of claim 1, wherein the bridge is an anodic bridge and is made of cellulose-based material provided with sulphonic acid groups.

8. The electrode bridge of claim 1, wherein the bridge is an anodic bridge and is made of polyacrylamide provided with acid acrylamido derivatives.

9. A kit comprising one or more electrode bridge(s) of claim 1 and one or more IPG gel(s).

10. The kit of claim 9, wherein the IPG gel comprise an acidic pH (below pH 4).

11. The kit of claim 9, wherein the bridge is an anodic bridge comprising polyacrylamide provided with acid acrylamido derivatives.

* * * * *